United States Patent [19]
Vashitz et al.

[11] Patent Number: 5,539,139
[45] Date of Patent: Jul. 23, 1996

[54] GRANULATED FATTY ALCOHOL SULFATE PRODUCTS

[75] Inventors: Oded Vashitz; Amatzia Galler, both of Kibbutz Dalia, Israel

[73] Assignee: Zohar Detergent Factory, Israel

[21] Appl. No.: 377,659

[22] Filed: Jan. 24, 1995

[30] Foreign Application Priority Data

Jan. 31, 1994 [IL] Israel ........................ 108500

[51] Int. Cl.$^6$ .................................................. C07C 305/00
[52] U.S. Cl. .................................................. 558/38
[58] Field of Search .................................. 558/38

[56] References Cited

FOREIGN PATENT DOCUMENTS

0544365A1 6/1993 European Pat. Off. .
4204090 8/1993 Germany .

Primary Examiner—Johann Richter
Assistant Examiner—Laura L. Stockton
Attorney, Agent, or Firm—Merchant, Gould Smith, Edell, Welter & Schmidt

[57] ABSTRACT

A granulated fatty alcohol sulphate is characterized by a bulk density greater than 600 g/lit when no consolidation stress is imparted, it has a particle size-distribution such that at least 15% of the particles are larger than 1000 μm, and less than 10% of the particles are smaller than 250 μm, and has a bulk density which is dependent on the consolidation stress in the range 200 kg/cm$^2$ to at least 750 kg/cm$^2$.

7 Claims, 4 Drawing Sheets

GRANULATED FATTY ALCOHOL SULFATE PRODUCTS

FIELD OF THE INVENTION

The present invention relates to novel free-flowing concentrated fatty alcohol sulphates in granular form and to a process for their production.

BACKGROUND OF THE INVENTION

Fatty alcohol sulphates (FAS) are surfactants used for various applications, such as in synthetic soaps, toothpastes, cosmetics and other personal care products, emulsifying agents in polymerization processes, and household and industrial cleaning formulations. The process for the manufacturing of concentrated fatty alcohol sulphates which is known in the art consists of three consecutive steps, namely: 1) sulphation of the organic raw material, which is an alcohol of natural or synthetic source having a chain length of $C_8$ to $C_{20}$, by $SO_3$; 2) neutralization of the unstable acidic alcohol sulphate produced to form stable salt of the cation used (e.g., sodium, potassium, ammonium, magnesium, or mono-, di- or triethanol amines); and 3) drying. The neutralized product can be processed as a dilute liquid with 25–35% active material, or as a concentrated semi-solid with 60–75% active material, where the active agent may be, for example, sodium alcohol sulphate. The final stage of the process is the drying of the neutralized salts of FAS, to obtain the non-sticky solid form.

THE PRIOR ART

The prior art products present several drawbacks: they are friable, very dusty, and prone to serious processing problems associated with low density. Certain ecological problems have also been noted, as the result of the small particles carry-over.

In order to overcome the known problems, manufacturers had to introduce a subsequent stage of compacting or kneading the dry solids into needles of various dimensions. Thus, the dustiness and irritation of the material is somewhat reduced. However, this stage also substantially affects the rate of water dissolution of the product.

SUMMARY OF THE INVENTION

It is an object of the invention to provide an improved product, which overcomes the drawback of prior art granular fatty alcohol sulphates.

It is another object of the invention to provide a process for the manufacturing of such improved granular products, which is simple, inexpensive and industrially applicable.

Other objectives of the invention will become apparent as the description proceeds.

In order to overcome the problems of the known art detailed above, the invention provides a novel product of improved properties. The product of the invention is obtained through a manufacturing method involving two first stages, namely the sulphation and neutralization, which are carried out in a conventional way. The third stage, which is the drying process of the invention, as described below, leads to a final product which is physically different from presently available products.

The granulated fatty alcohol sulphate of the invention is characterized in that:

It has a bulk density greater than 600 g/lit when no consolidation stress is imparted;

It has a particle size-distribution such that at least 15% of the particles are larger than 1000 μm, and less than 10% of the particles are smaller than 250 μm; and It has a bulk density which is dependent on the consolidation stress in the range 200 kg/cm² to at least 750 kg/cm².

"Consolidation stress" is meant to indicate the stress which is a result of a pressure gradient developed on the particle during flow.

According to a preferred embodiment of the invention, the granulated fatty alcohol sulphate of the invention has:

a bulk density of about 700 g/lit;

a particle size-distribution such that about 17% of the material is larger than 1000 μm, and less than 8% of the material is smaller than 250 μm.

Unless otherwise indicated, all percentages given herein are by weight. The product according to the invention contains sodium or sodium/potassium salts of lauryl alcohol sulphate, having the structural formula of $ROSO_3M$ wherein R is $C_{10}$–$C_{22}$ alkyl and M may be selected from among Na, K, Mg, Na/K, ammonium, mono-, di- or triethanol amines. The alkyl range used as well as the Na/K ratio and the molecular weight of the resulting product may be varied according to the end product requirements. Illustrative examples of such alkyls are Lorol $C_{10}$–$C_{22}$, Lorol $C_{12}$, Lorol Spezial ($C_{12}$–$C_{14}$), Lorol V ($C_{12}$–$C_{16}$), Lorol $C_{12}$–$C_{18}$, Stenol 1822A ($C_{18}$–$C_{22}$)(all of these ex. Henkel), and the like.

The granulated fatty alcohol sulphate according to the invention, as stated above, exhibits excellent dissolution properties in water. Furthermore, the granular product obtained according to the invention is free-flowing, and is very convenient to use as a raw material in further processing.

Illustrative examples of product density, as measured for several samples having various percentages of dry matter are:

| Bulk Density (gr/cc) | % Dry Matter |
| --- | --- |
| 0.60 | 95.8 |
| 0.72 | 99.4 |
| 0.80 | 99.4 |
| 0.86 | 97.0 |
| 0.88 | 99.5 |

All the above and other characteristics and advantages of the invention will be better understood through the following illustrative and non-limitative description of preferred embodiments.

DETAILED DESCRIPTION OF PREFERRED EMBODIMENTS

The improved granulated fatty alcohol sulphates of the invention are obtained by slowly drying under vacuum a material consisting essentially of fatty alcohol sulphate, having a total dry matter content between 62 wt % and 80 wt %, while solid mixing means are provided to mechanically mix the drying mixture during the drying process. The remaining 38–20 wt of dry matter typically consists of a solvent or a mixture of solvents, unsulphated fatty alcohol (0.5–2.0 wt %), NaCl (0–0.5 wt %) and $Na_2SO_4$ (1.0 wt %).

According to a preferred embodiment of the invention the solvent consists essentially of water. According to another preferred embodiment of the invention, the solvent is a mixture of water and an organic solvent. Suitable organic solvents that can be used are, e.g., ethanol, propanol, isopropanol, acetone, methyl ethyl ketone, polyethylene glycol or the like.

According to another preferred embodiment of the invention, additives and components like co-surfactants or builders may be added to the product. Suitable co-surfactants that can be used are anionic surfactants, e.g., dodecyl benzene sulphonate and toluene sulphonate, nonionic surfactants, e.g., ethoxylated fatty alcohols, and cationic surfactants, e.g., quaternary amido compounds, and the like.

As will be appreciated by the skilled person, the advantages of the invention are achieved by the combined effect of a slow drying, such as can be achieved by vacuum drying in rotary equipment, and mechanical mixing of the slurry/ solid material during drying, which results in the granulation being effected during drying. In one preferred embodiment of the invention the vacuum is maintained at a level comprised between 5 and 60 mbar, absolute pressure. Other vacuum levels can of course be used, but they may be needlessly deep, or may require too long drying times to be operated with high economic advantage and, therefore, are not preferred, but they of course are within the ambit of the invention.

According to a specific preferred embodiment of the invention the process is carried out in a mixing chamber coupled to vacuum generating means. In one embodiment of the invention the mixing means comprise scraper blades moving near the walls of the mixing chamber. Preferably—but not limitatively—the distance between the scraper blades and the wall is between 0.1 and 10 mm, and the scraper blades rotate at a speed between 10 and 150 rpm.

The actual heating method is not essential to the invention, and any suitable heating method and apparatus can be employed. One convenient heating method, however, is that in which heat is supplied to the material to be dried by a heating jacket provided around the drying chamber.

As will be apparent to the skilled person, the invention is not limited to any specific fatty alcohol sulphate. Preferred fatty alcohols are the $C_{10}$–$C_{22}$ alcohols, e.g. sodium lauryl sulphate.

EXAMPLE 1

Figure 2:
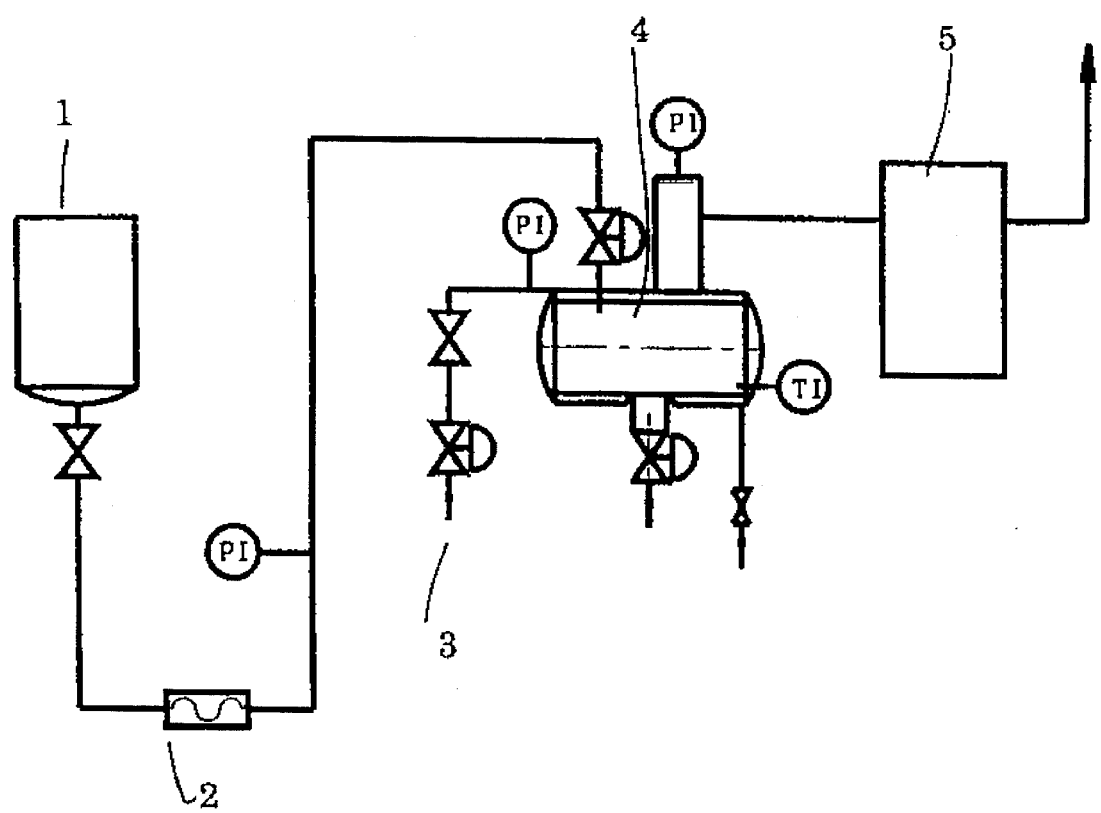
FIG. 2 shows the drying and granulating equipment used in the experiments of Examples 1 and 2.

The arrangement shown in FIG. 2 was used in this experiment. The product is transferred from a supply tank 1, by using a pump 2, to a mixer dryer, 4. The heat required in the process is supplied by the heating medium 3, introduced into the dryer. The whole process is carried out under sub-atmospheric pressure, which is maintained by the vacuum system 5.

Figure 1:
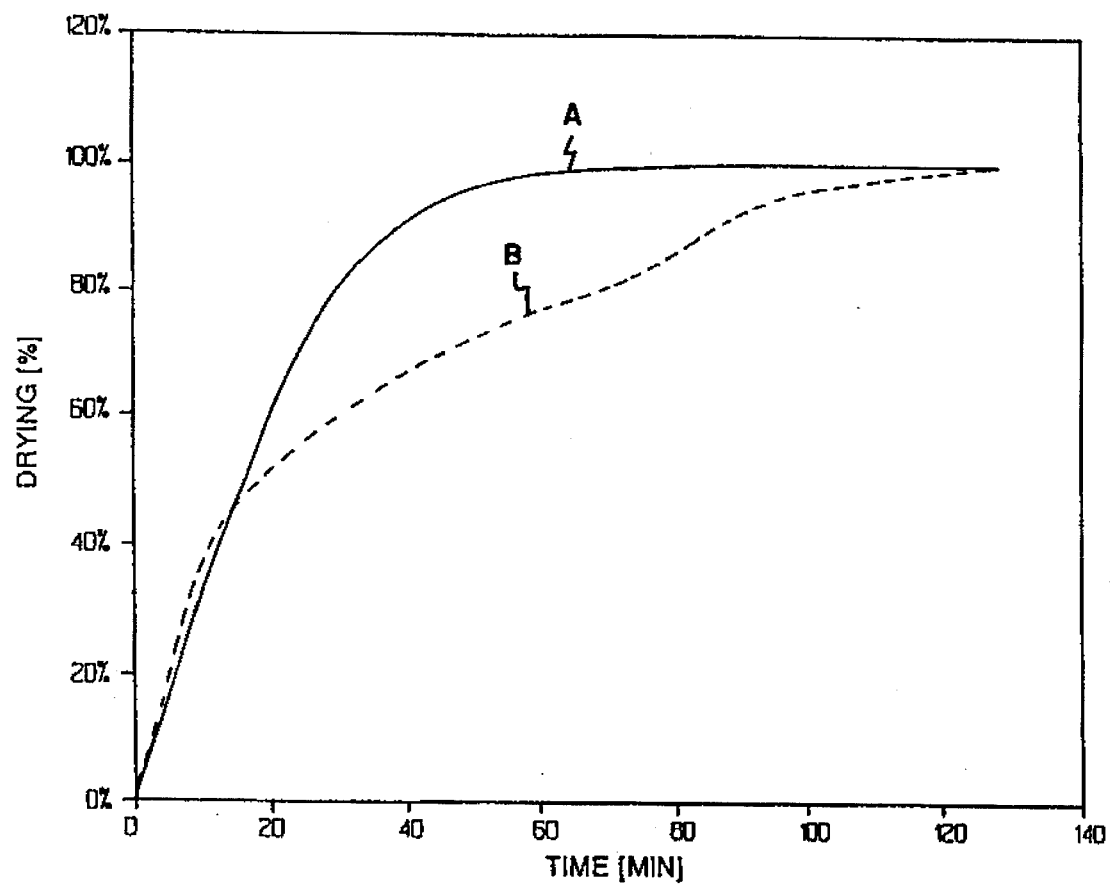
FIG. 1 shows the rate of drying obtained in Examples 1 and 2, wherein line A represents the drying rate of LAS NP (Example 1) and line B represents the drying rate of LAS NP+IPA (Example 2).

A 300 liter horizontal, jacketed drying chamber with rotary mixing blades was filled with 60 kg of Zoharpon LAS 70, containing sodium salt of lauryl alcohol sulphate. The structural formula of Zoharpon LAS 70 is $ROSO_3M$, wherein R is alkyl $C_{12}$–$C_{16}$ and M is Na. Stem was applied in the jacket and vacuuming was gradually increased until the moisture content of the product reached 1%. The actual rate of drying is shown in FIG. 1, in which the amount of water drawn from the sample is given as a function of time (line A).

Figure 3:
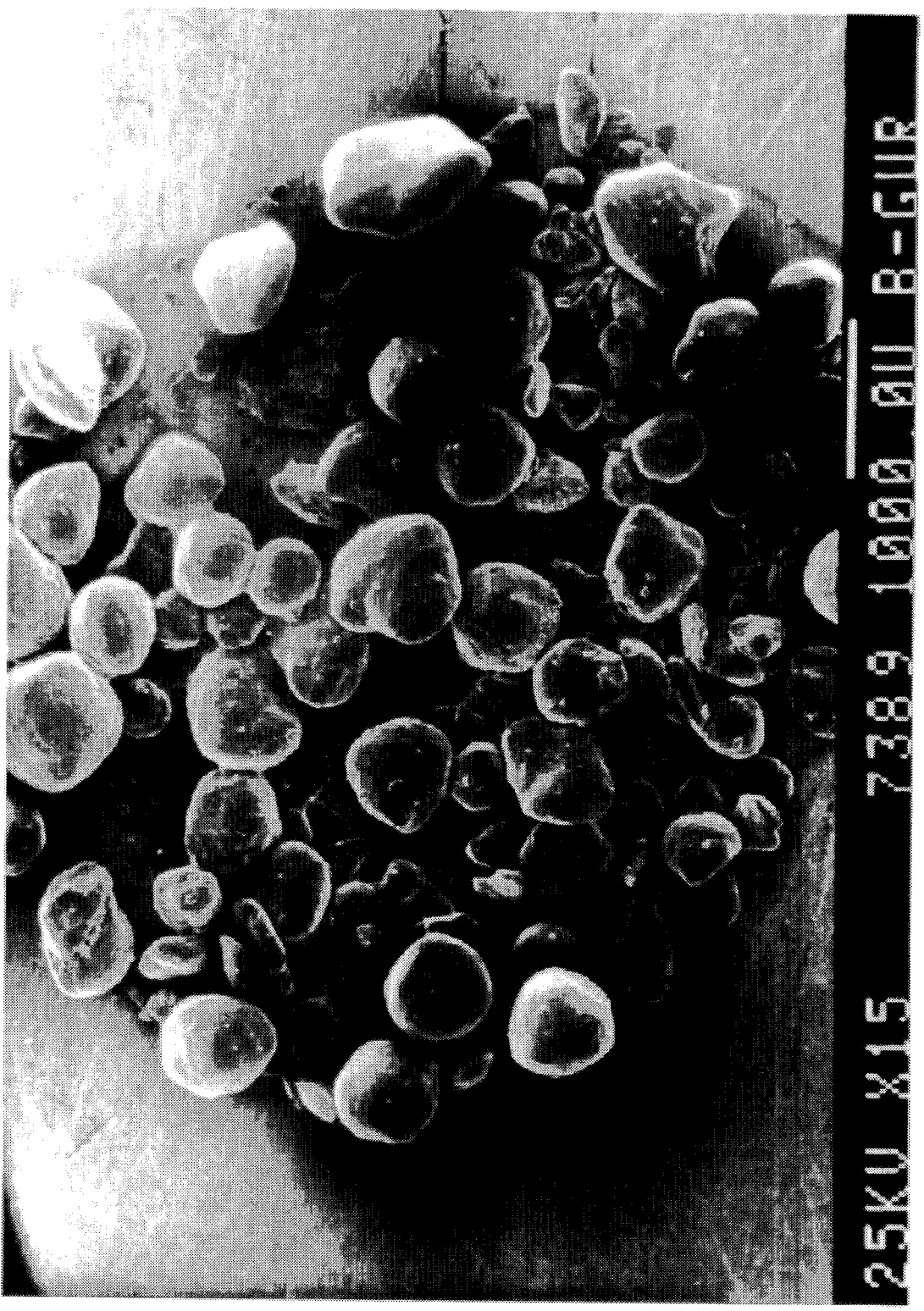
FIG. 3 shows SEM micrographs of particles obtained in Example 1, using X15 magnification.
Figure 4:
FIG. 4 shows SEM micrographs of particles obtained in Example 1, using X55 magnification.

The resulting material was characterized as follows:

bulk density: 720 g/lit.

water dissolution time of 2.05 min. at 20° C.

particle size distribution: as shown in Table I below.

two peaks in the X-ray analysis (CuKα, 40KV, 18mA), in the angle range $5° < 2\theta < 8°$, one at about 6.5° and the second at about 7.8°.

the particles obtained had a spherical form, as may be seen in FIGS. 3 and 4.

As may be seen from FIGS. 3 and 4, the product obtained has a polycrystalline structure composed essentially of round particles having a smooth surface.

The product was compared with a commercially available product (Texapon ZHK, ex Henkel), which is a sodium lauryl sulphate having a density of 0.21–0.28 gr/cc, and which comprises a $C_{12}$–$C_{18}$alkyl, and the corresponding results are reported in Table I below:

TABLE I

| Size (μm) | Zoharpon LAS NP | Texapon ZHK |
|---|---|---|
| >1000 | 17.28% | 0.1% |
| 850–1000 | 15.46% | 0.19% |
| 710–850 | 10.66% | 0.3% |
| 600–710 | 11.8% | 0.49% |
| 500–600 | 11.4% | 3.14% |
| 300–500 | 24.5% | 26.99% |
| 250–300 | 1.1% | 19.53% |
| 150–250 | 5.6% | 25.61% |
| 45–150 | 2.1% | 23.45% |
| <45 | 0.1% | 0.2% |
| TOTAL: | 100.00% | 100.00% |

EXAMPLE 2

Example 1 was repeated, but 20 liters of isopropyl alcohol were added to 60 kg of Zoharpon LAS 70, before drying, and the two materials were mixed. The drying rate of the solution in said chamber is given in FIG. 1 (line B), as in the previous example.

EXAMPLE 3

Rate of Dissolution in Water

The following experiment was carried out to compare the rate of dissolution of a product according to the invention with the commercially available product Texapon ZHK (ex Henkel). The conditions and results were as follows: 3 Wt % of the tested material were added to water at 20° C. and were stirred using a magnetic stirrer. The materials used were as in Example 2, and the time required to reach a clear solution was measured. Results were as follows:

| Material | Dissolution time [min] | Dissolution rate [gr/gr water · min] |
|---|---|---|
| ZOHARPON LAS NP | 2.05 | 0.015 |
| TEXAPON K12 (GRANULAR) | 5.0 | 0.006 |

EXAMPLE 4

The following experiment was carried out to compare the built density of a product according to the invention with the commercially available product Texapon ZHK (ex Henkel).

The samples were compared under three stress ranges: no stress, low stress and high stress. The results obtained for the bulk density in g/lit are given in Table II.

TABLE II

| stress applied | Bulk Density (g/lit) | |
|---|---|---|
| [kg/cm] | Zoharpon LAS NP | Texapon ZHK |
| no stress | 696 | 294 |
| 0.077 | 727 | 319 |
| 0.4 | 739 | 347 |
| 200 | 1320 | 1186 |
| 999 | 1367 | 1186 |

EXAMPLE 5

In order to compare the flowability of a product according to the invention with Texapon ZHK, the following shear test was conducted.

The test was carried out using a bulk of particles introduced into a shear tester. The shear tester was used for the measurement of the angle of the wall friction ($\Phi'$). The procedure used to measure the horizontal forces required sliding a sample of bulk solid under a given normal load across a piece of material.

$$\text{Hence } \tan \Phi' = \frac{\text{horizontal force}}{\text{normal load}}$$

Knowing tan $\Phi'$, it is possible to assess whether or not mass flow is possible in a particular set up. The consolidation force applied was in the range 0.43 kg. to 20 kg. The actual force required for the shear was measured and subsequently used for calculating the consolidation stresses, as well as angle of internal friction, unconfined yield strength and major consolidation stress.

The first set of tests was carded out when the consolidation time was equal to zero. The second test was done after 24 hours of consolidation under consolidation forces of 0.84 kg. to 14 kg.

From the results of these tests, the flow function, FF, has been calculated. The flow function is defined as the ratio of major consolidation stress ($W_m$) to the unconfined yield strength ($W_c$). Wherein, "unconfined yield strength" is meant to indicate the major consolidation stress when the shear stress is equal to zero. The flow function is used to characterize

| FF < 2 | non-flowable solids (sticky) |
| 2 < FF < 4 | cohesive (flowable) |
| 4 < FF < 10 | easy flowing |
| FF > 10 | free flowing |

The results obtained are presented in Table III.

TABLE III

| Consolidation force [kg] | Consolidation time [hr.] | FLOW FUNCTION FF | |
|---|---|---|---|
| | | Zoharpon LAS NP | Texapon ZHK |
| 0.84 | 0 | 5.17 | 5.81 |
| | 24 | 0.56 | 0.46 |
| 2.8 | 0 | 5.18 | 6.11 |
| | 24 | 0.93 | 0.76 |
| 7.0 | 0 | 5.84 | 6.44 |
| | 24 | 1.48 | 1.26 |
| 14.0 | 0 | 8.32 | 8.18 |
| | 24 | 2.48 | 1.88 |
| internal sheer angle | | 25.5 | 37.2 |

The above descriptions and examples have been given for the purpose of illustration, and are not intended to limit the invention in any way. Many modifications can be effected in the various starting materials, additives and process conditions, all without exceeding the scope of the invention.

We claim:

1. A granulated fatty alcohol sulphate, characterized in that:

It has a bulk density greater than 600 g/lit when no consolidation stress is imparted;

It has a particle size-distribution such that at least 15% of the particles are larger than 1000 μm, and less than 10% of particles are smaller than 250 μm; and It has a bulk density which is dependent on the consolidation stress in the range 200 kg/cm² to at least 750 kg/cm².

2. A granulated fatty alcohol sulphate according to claim 1, having an internal shear angle of no more than 30°.

3. A granulated fatty alcohol sulphate according to claim 1, of the chemical formula of $ROSO_3M$, wherein R is $C_{10}$–$C_{22}$ alkyl and M is selected from among Na, K, Na/K, Mg, ammonium, mono-, di- or triethanol amines.

4. A granulated fatty alcohol sulphate according to claim 1, characterized by:

a bulk density of about 700 g/lit; and a particle size-distribution such that about 17% of particles is larger than 1000 μm, and less than 8% is smaller than 250 μm.

5. A granulated fatty alcohol sulphate according to claim 1, having two peaks in the X-ray spectrum (CuKα, 40 KV, 18 mA), in the angle range 5°<2ϑ<8°.

6. A granulated fatty alcohol sulphate of claim 5, wherein the first peak is at about 6.5° and the second at about 7.8°.

7. A granulated fatty alcohol sulphate according to claim 1, having a dissolution rate of 0.015 gr/gr water.min at 20° C.

* * * * *

UNITED STATES PATENT AND TRADEMARK OFFICE
CERTIFICATE OF CORRECTION

PATENT NO. : 5,539,139

DATED : July 23, 1996

INVENTOR(S) : Vashitz et al.

It is certified that error appears in the above-identified patent and that said Letters Patent is hereby corrected as shown below:

In column 4, line 5, "Stem" should read --Steam--.

In column 4, line 33, "(um)" should read --(µM)--

In column 5, line 12, "built" should read --bulk--.

In column 5, line 51, "carded" should read --carried--.

In column 5, line 62, insert --solids according to the following regimes:-- after the word "characterize".

In column 6, line 59, insert --about-- after the word "of".

Signed and Sealed this

Twenty-fourth Day of June, 1997

Attest:

BRUCE LEHMAN

*Attesting Officer*  *Commissioner of Patents and Trademarks*